United States Patent
Dafni et al.

[11] Patent Number: 5,966,422
[45] Date of Patent: Oct. 12, 1999

[54] MULTIPLE SOURCE CT SCANNER

[75] Inventors: Ehud Dafni, Caesarea; David Ruimi, Natanya, both of Israel

[73] Assignee: Picker Medical Systems, Ltd., Haifa, Israel

[21] Appl. No.: 08/903,761

[22] Filed: Jul. 31, 1997

Related U.S. Application Data

[63] Continuation-in-part of application No. 08/556,824, Nov. 2, 1995, which is a continuation of application No. 07/915,549, Jul. 20, 1992, abandoned.

[30] Foreign Application Priority Data

Aug. 1, 1996 [IL] Israel ......................................... 118989

[51] Int. Cl.⁶ ............................................. A61B 6/03
[52] U.S. Cl. ................................................. 378/9; 378/15
[58] Field of Search .................................... 378/9, 15

[56] References Cited

U.S. PATENT DOCUMENTS

| | | | |
|---|---|---|---|
| 4,196,352 | 4/1980 | Berninger et al. | 378/7 |
| 4,669,103 | 5/1987 | Barnea | 378/10 |
| 5,012,498 | 4/1991 | Cuzin et al. | 378/22 |
| 5,228,069 | 7/1993 | Arenson et al. | 378/19 |
| 5,241,576 | 8/1993 | Lonn | 378/19 |
| 5,262,946 | 11/1993 | Heuscher | 378/15 |
| 5,291,402 | 3/1994 | Pfoh | 378/13 |
| 5,335,255 | 8/1994 | Seppi et al. | 378/4 |
| 5,430,784 | 7/1995 | Ribner et al. | 378/19 |
| 5,469,487 | 11/1995 | Hu | 378/9 |
| 5,485,493 | 1/1996 | Heuscher et al. | 378/15 |
| 5,604,778 | 2/1997 | Polacin et al. | 378/9 |
| 5,805,663 | 9/1998 | Mihara | 378/98.2 |

*Primary Examiner*—David Vernon Bruce
*Attorney, Agent, or Firm*—Fenster & Company Patent Attorneys, Ltd.

[57] ABSTRACT

A Computerized Tomographic (CT) helical scanner system including multiple, separate x-ray sources mounted on the same gantry, each irradiating different two-dimensional detectors at any given time to simultaneously acquire data from multiple slices and combining the data obtained from the multiple slices to provide images either of individual slices or combined slices.

36 Claims, 13 Drawing Sheets

TYPICAL SYSTEM OF COORDINATES

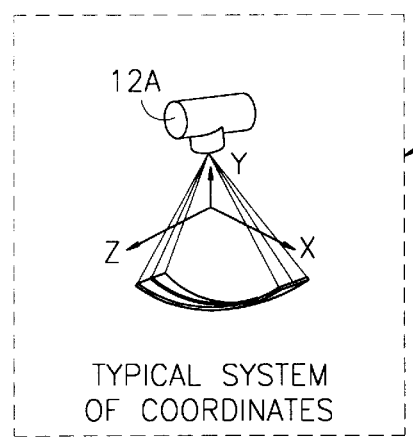
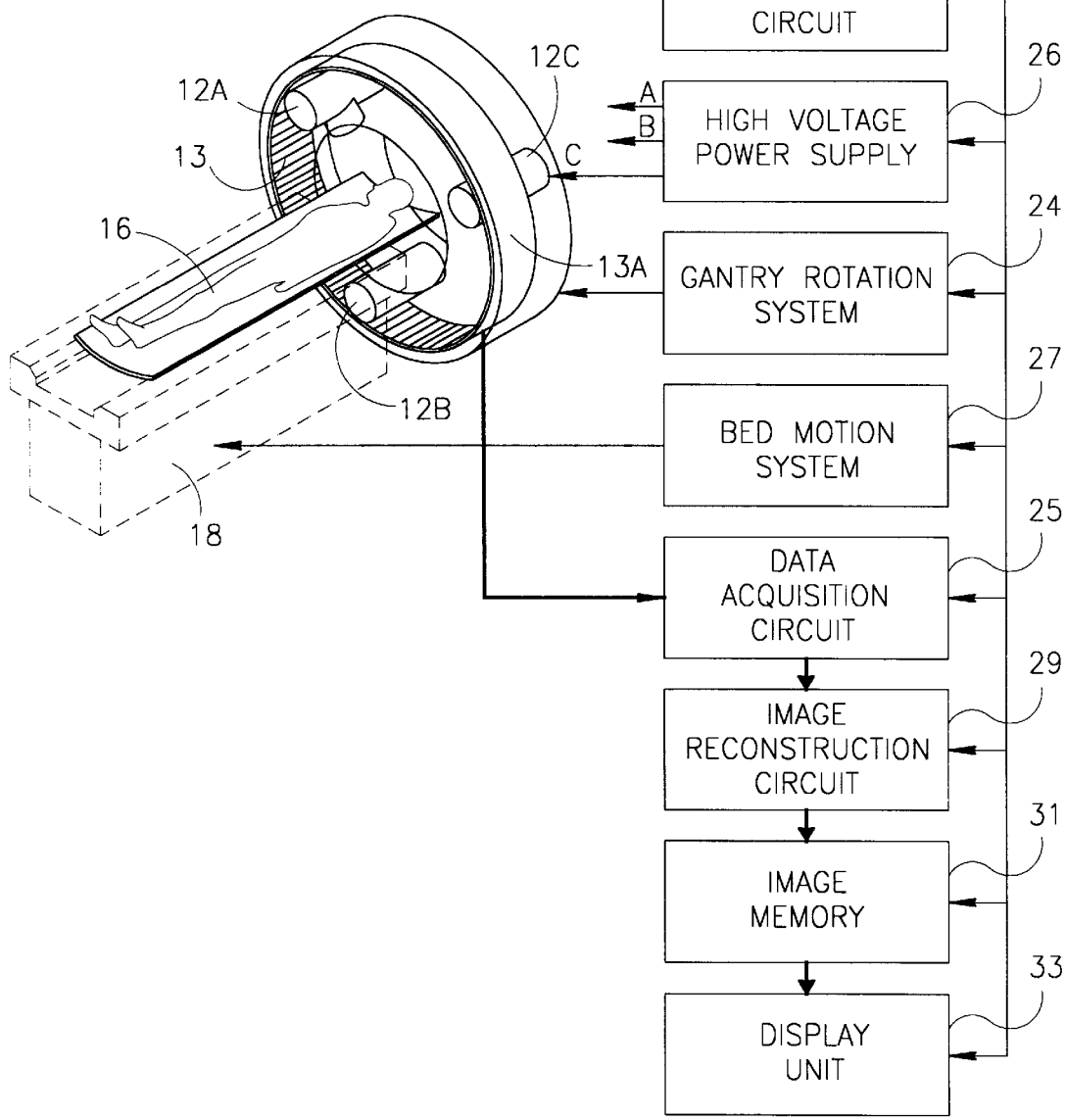

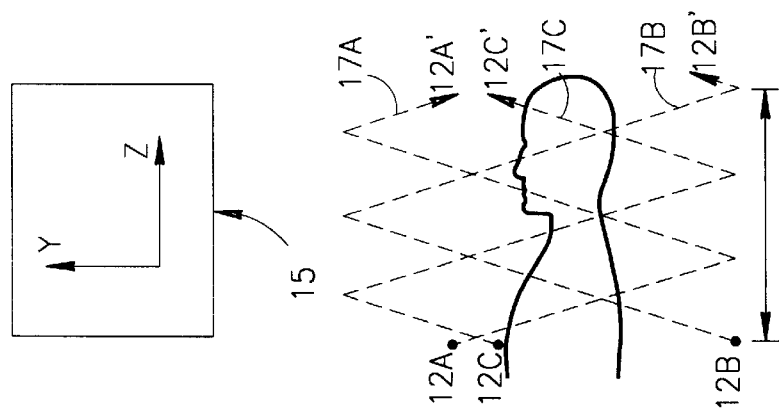
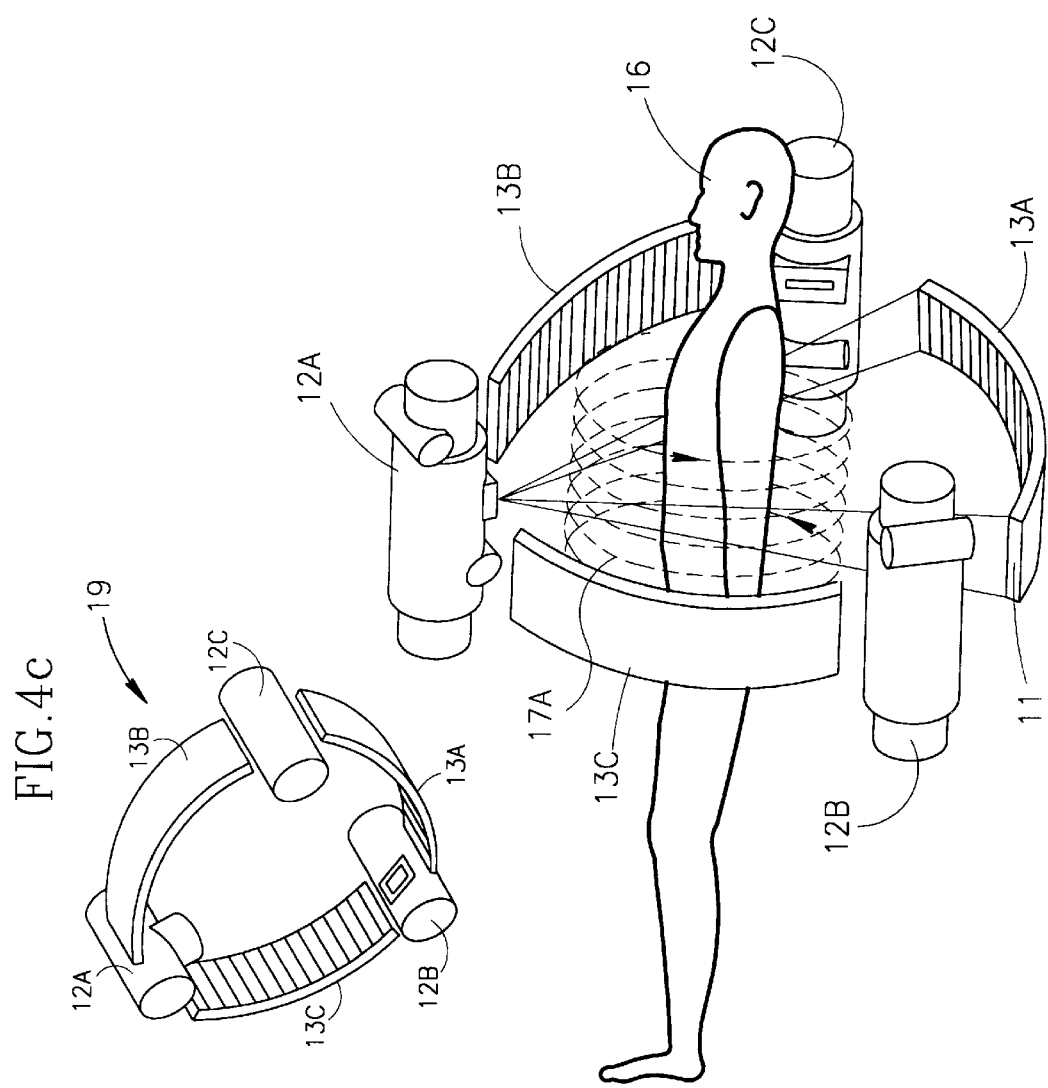
FIG. 4b
FIG. 4a
FIG. 4c

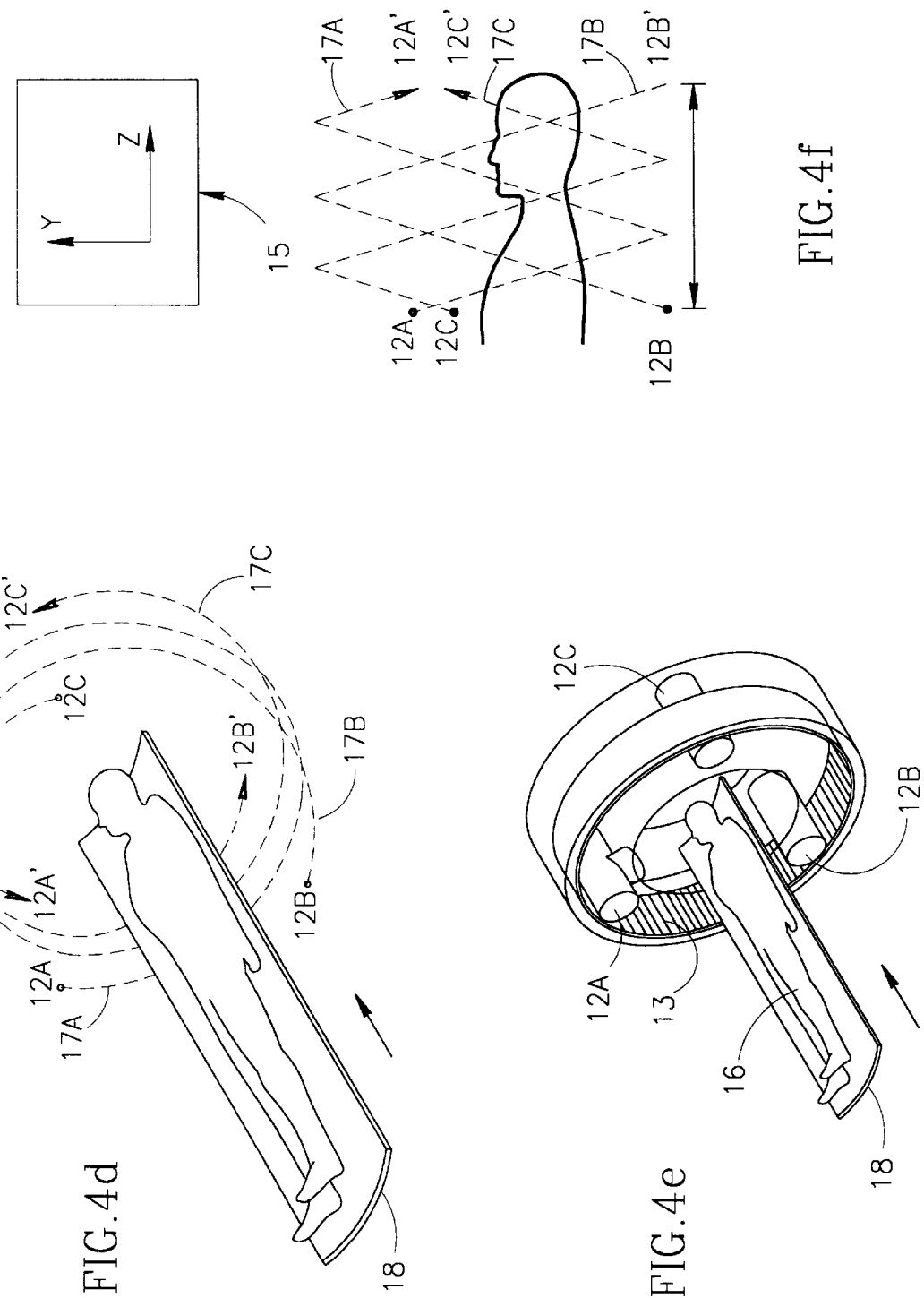

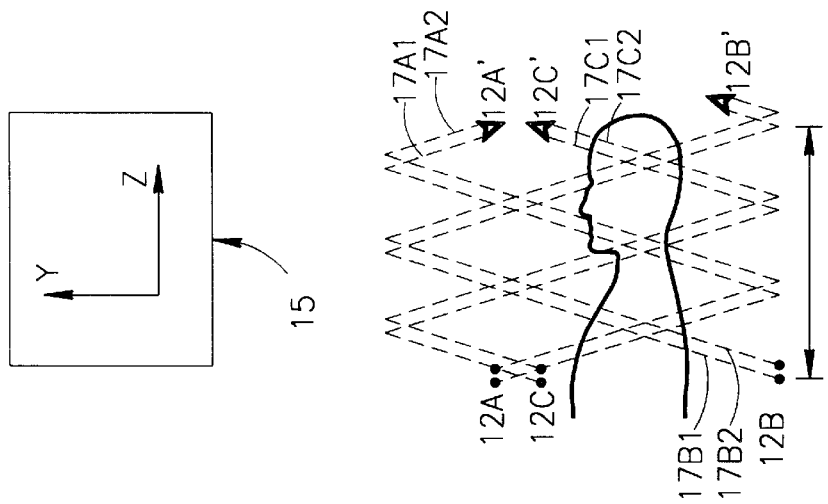
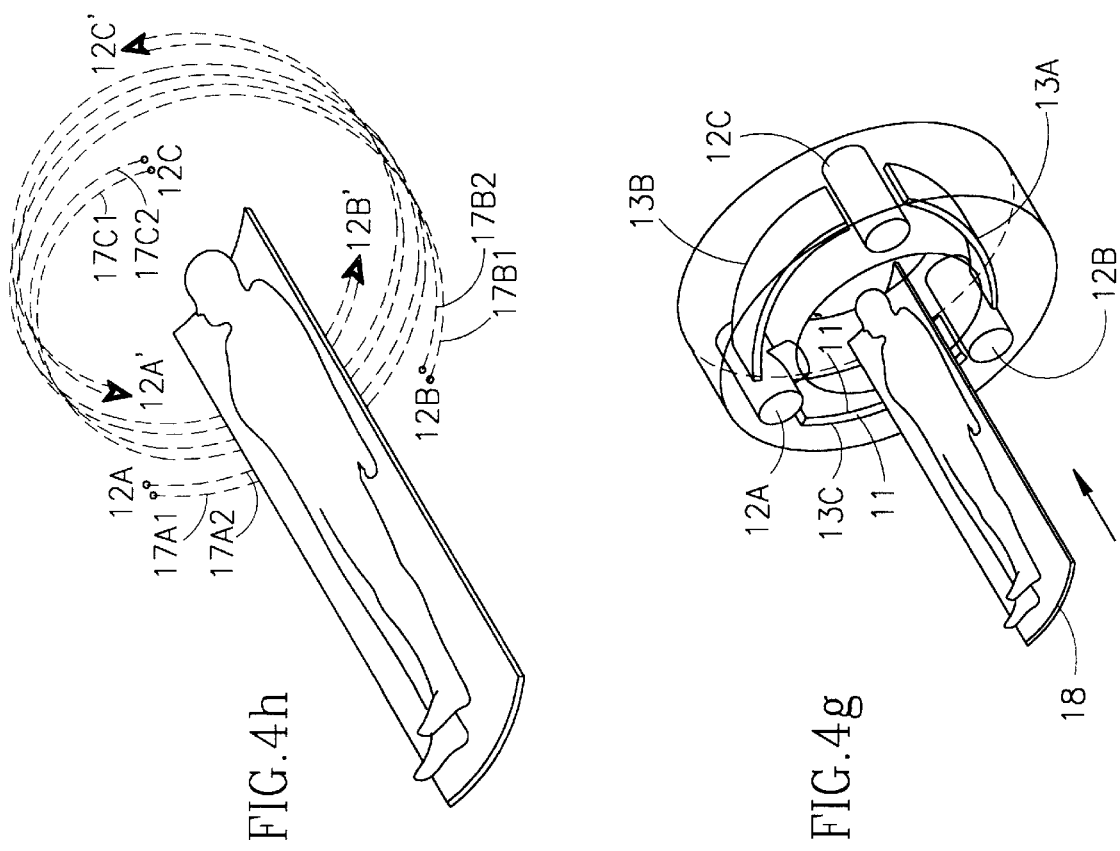
FIG. 4i
FIG. 4h
FIG. 4g

MULTIPLE SOURCE CT SCANNER

RELATED APPLICATIONS

This application is a continuation-in-part of U.S. patent application Ser. No. 08/556,824, filed Nov. 2, 1995 which is a continuation of U.S. patent application Ser. No. 07/915,549, filed Jul. 20, 1992 now abandoned, the disclosures of which are incorporated herein by reference.

FIELD OF THE INVENTION

This invention is concerned with computerized tomographic (CT) systems and more particularly with systems equipped with multiple sources of radiation located on a single gantry on which there may also be multiple arrays of detector elements.

BACKGROUND OF THE INVENTION

CT systems produce planar images along imaginary cuts through a subject. Each cut is referred to as a slice. Scanners in general comprise an X-ray source which revolves about an imaginary axis through a subject. The X-rays, after passing through the subject, impinge on an opposing array of detectors, which may also be revolving. Data for reconstruction of a single image includes a set of views corresponding to different projection angles, each view comprising radiation intensity data measured by detector elements at a particular projection angle.

A prior art CT study of a subject for obtaining successive planar images includes the following steps:

1. Putting the patient on the bed in a CT system gantry.
2. Scanning the patient. The scan includes the revolution of the X-ray source about the subject and acquisition of radiation intensity data per detector element per angle of revolution of the X-ray source.
3. Reconstructing the image. Optional display, archiving and/or filming.
4. Incrementing the bed to the position of the next slice.

Steps 2–4 are repeated as long as more slices are required. Step 3 may be concurrent with steps 2 and 4, but step 4 must be successive to step 2. Step 4 involves acceleration and de-acceleration of the bed if the bed is stationary during the scan such as when successive planar images are acquired. Step 2 may involve acceleration and de-acceleration of the gantry to the proper rotational speed. Gantry acceleration and de-acceleration may, however, be circumvented by using a continuous rotation scanner such as provided, e.g., by slip-ring technology.

An ubiquitous problem encountered by CT systems is that a complete 360° rotation of the gantry is required to achieve a high quality image. At least 180° of rotation is required to achieve a full set of projections. One solution is a multiple source X-ray tomograph such as described e.g. in U.S. Pat. No. 4,991,190 where high resolution or high speed scans may be achieved.

Other problems occur with the prior art CT scanners used to obtain a series of planar images. For example, the successive nature of the scanning process described hereinabove, prolongs the time during which the subject is imaged. The longer throughput time results in greater patient discomfort. The bed acceleration and de-acceleration add to the discomfort of the patient. Further, the patient is required to adjust his breathing cycle to the scanning rate so as to reduce motion related image artifacts. When the examination period is longer, the breath control is more difficult resulting in more patient motion, both during scans and between scans. Patient motion, voluntary and involuntary, between scans decreases the repeatability that is desired between adjacent slices. In particular, oblique reformatting and 3-D images formed from series of planar images are adversely affected.

To overcome these problems, helical or spiral scanning systems have been investigated and developed. This type of scanning is described in the following references:

1. P. Slavin, U.S. Pat. No. 3,432,657 (1969).
2. I. Mori, U.S. Pat. No. 4,630,202 (1986).
3. H. Nishimura, U.S. Pat. No. 4,789,929 (1988).
4. W. A. Kalandar, P. Vock and W. Seissler in Advances in CT (Springer-Verlag, Berlin, Heidelberg 1990, pp. 55–64).
5. C. R. Crawford and H. F. King, Med. Phys. 1796), (1990) pp. 967–982 and reference therein.

Essentially, with helical scanning scanners, the subject is continuously scanned while the gantry makes multiple rotations about the subject and the bed is moved relative to the gantry along the axis of rotation simultaneously with the rotation. Images of successive slices are recontructed from sets of views using well known recontruction algorithms.

In conventional non-helical; i.e., stationary bed CT scans made to image successive slices, the different views making up the different sets correspond to projections within the same plane. On the other hand, in the helical scans the different views making up the different sets correspond to projections in different planes.

Therefore, non-modified conventional reconstruction yields artifacts; i.e., highly distorted images. To prevent such artifacts, the raw data is reformatted before backprojection into single plane data sets by interpolating between data measured at the same gantry angle but at different subject positions, providing data of different planes.

The theoretical slice sensitivity profile is defined as the response of the scanner to a small homogeneous object as a function of the object position along the axial direction. The slice width is defined as a full width at half maximum (FWHM) of the slice sensitivity profile.

In stationary-bed CT scans, the slice width is determined by collimators limiting the beam width or the length of the detector elements in the axial direction. In helical scans, data from different planes through the subject are mixed and the slice sensitivity profile is smeared. Therefore, the FWHM of the profile tends to be larger in a helical scan than in a stationary-bed scan for a given collimator setting. Also, the ratio between the full width at tenth maximum (FWTM) and the FWHM of the sensitivity profile, which as a measure of the quality of the slice width, is severely degraded.

Various schemes to improve the slice sensitivity profile in helican scans are discussed in the references cited hereinabove. These include:

1. Linear and non-linear interpolation schemes;
2. Variable bed speeds associated with appropriate interpolation schemes; and
3. Reducing the bed speed so that the bed moves less than a whole slice width within a single gantry revolution.
4. Reconstruction using data from only 180° of rotation before the desired position and 180° of rotation after the desired position.

Non of these schemes, however, provides images of the quality obtained in prior art stationary bed CT systems for a given radiation dose applied to the subject. Furthermore, because of the increased time length of exposure required in helical scans, the available X-ray intensity is likely to be less than in stationary bed CT systems, thus further decreasing image quality.

One possible solution to the problems encountered in prior art X-ray computed tomography is a multiple slice tomograph as taught in the above referred to Patent Application. The present invention provides both an alternative solution and an additional solution.

BRIEF DESCRIPTION OF THE INVENTION

Accordingly, it is an object of the present invention to overcome the prior art problems general to CT scanning and specific to helical scanning. It is a related object of the present invention to improve prior art helical scanning systems.

In accordance with one preferred embodiment of the present invention, a unique CT scanner system is provided, said system comprising:

a gantry, a bed for supporting a scanned subject, multiple X-ray sources mounted on said gantry, an X-ray detector array on a side of the subject opposite to each of the X-ray sources, said detector arrays comprising detector elements for simultaneously detecting X-rays from multiple sources that have traversed one or multiple planar sections of said subject to acquire radiation density data, rotary drive mechanisms for rotating the X-ray sources about the subject, the detector arrays may be rotating opposite to the X-ray sources (3rd generation CT scanner) or stationary, (4th generation CT scanner), longitudinal drive mechanisms for causing relative motion in an axial direction between the bed and the gantry while the X-ray sources are revolving about the subject, and an image processor for reconstructing images from said data where said image processor includes a reformatting arrangement for reformatting the acquired data into single plane data by interpolating between data acquired by detector elements that may be exposed to different X-ray sources and/or to the same X-ray source.

According to a feature of the invention, the reformatting arrangement comprises elements for interpolating between data detected by the same and/or different detector elements in the same angular position during the revolution, but in different axial positions along the subject. The same angular position is understood herein to also include modular 180° and modular 360°.

According to another feature of the invention, the X-ray radiation originates from multiple sources at different angles around the gantry with detectors positioned on a side of the subject opposite to the X-ray sources.

According to yet another feature of the invention, the detector arrays rotate with and opposite to the X-ray sources.

According to still another feature of the invention, the detector arrays are stationary.

BRIEF DESCRIPTION OF THE DRAWINGS

The above mentioned and other objects and features of the present invention will be best understood when considered in the light of the following description made with reference to the accompanying drawings wherein:

FIG. 4a illustrates a helical scanner of the present invention with multiple X-ray sources and multiple arrays of single detector elements arranged in one plane.

FIG. 4b is a side view tracing the path of each of the X-ray sources in the scanner of FIG. 4a.

FIG. 4c illustrates a helical scanner showing the helical paths of the multiple sources; when each of the multiple sources has a single row detector array.

FIG. 4d is a pictorial view of the fourth generation scanner showing the multiple sources and the stationary ring array of detector, FIG. 4e is a side view of the helical paths of the multiple sources in the manner of FIG. 4d.

FIG. 4f is a pictorial view of the third generation scanner having multiple sources and detector arrays with multiple rows of detectors in the Z direction, FIG. 4g illustrates a helical scanner showing the helical paths of the multiple sources when each source has two row detector arrays in the Z direction;

FIG. 4h is a side view tracing the path of each of sources to the two row detector arrays in the Z direction of the scanner of FIG. 4g;

GENERAL DESCRIPTION

Figure 1B:
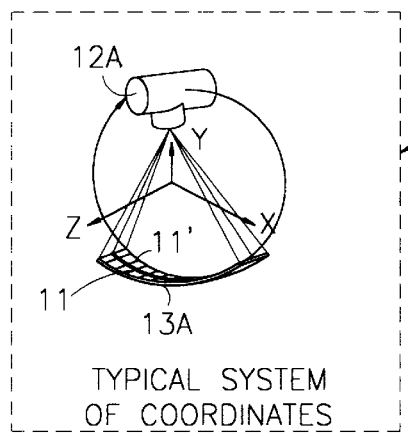
FIG. 1b is a pictorial block diagram showing an example of a fourth generation CT scanner according to the present invention.
Figure 1A:
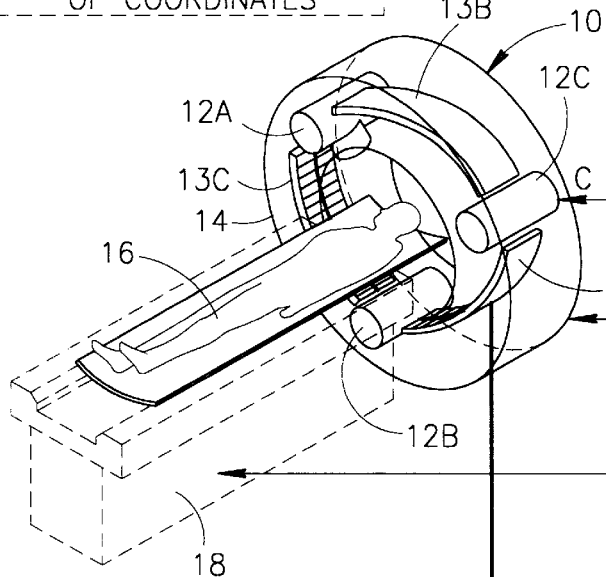
FIG. 1a is a pictorial-block diagram showing an example of a third generation CT scanner according to the present invention.
Figure 1A:
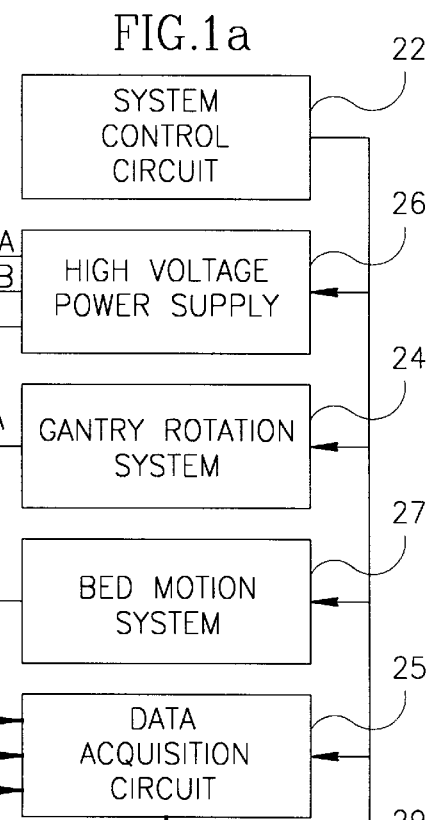
Figure 1C:
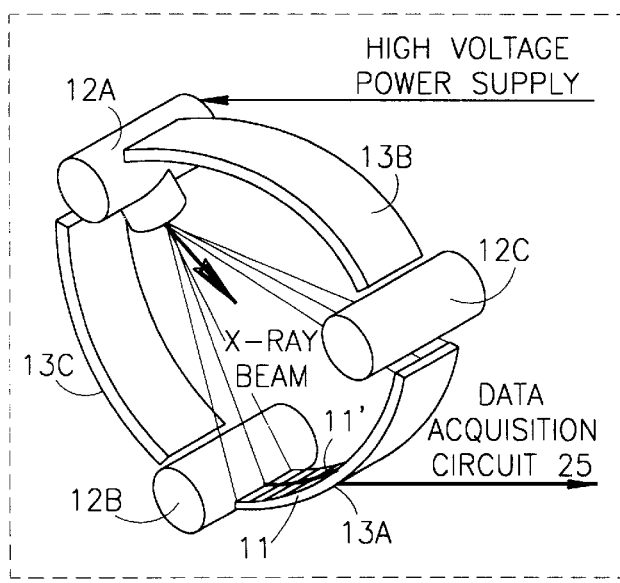

FIG. 1a is a general layout of a third generation (rotate-rotate) scanner 10 comprising three X-ray sources 12a, 12b, and 12c mounted onto a gantry 14. A subject 16 to be scanned is supported by means of a bed 18. Fan-shaped X-rays which traverse a planar section through the subject 16 are detected by detector arrays 13a, 13b and 13c.

Cartesian coordinate system 15 is defined in FIG. 1a. Therein the Z axis is along an imaginary longitudinal axis that is the rotational axis of the gantry. It may be coincidental to the longitudinal axis through the subject. For each X-ray source, there is a Y axis along a straight line from X-ray source to the center of revolution of gantry 14, and an X axis that is perpendicular to the above axes. As gantry 14 revolves about the Z axis, so does the coordinate system 15 relative to a stationary surrounding.

According to one embodiment of the present invention shown in FIG. 1a, there are three X-ray sources and opposing detector arrays denoted by letters a, b, and c. However, according to the invention the number of sources and detector arrays may each be different than three. Detector elements 11 shown, for example, data acquisition circuit 25, detect the X-rays that have passed through multiple planar sections in subject 16. The apparatus illustrated in FIG. 1a is referred to as multiple source, multiple slice CT scanner of the third generation type. The apparatus illustrated in FIG. 1b, which differs from that of FIG. 1a in that there are stationary detectors, is referred to as a multiple source, multiple slice CT scanner of the fourth generation type.

The various operations of the computerized tomography system 10 are controlled by means such as system control circuit 22. Thus, circuit 22 controls, among other things, the operation of the rotation system 24 of the gantry 14. More particularly, gantry 14 with X-ray sources 12a, 12b and 12c revolves about the Z axis powered and controlled by gantry rotation system 24 while the X-ray sources 12a, 12b and 12c are energized by high voltage power supply 26. Subject 16 is positioned within a central aperture of gantry 14 by means of bed motion control system 27.

The intensity of the radiation after its traversal of the subject 16 is detected by detector arrays 13 and acquired by data acquisition circuit 25. Radiation intensity data from rays traversing subject 16 over a range of at least 180° in the gantry revolution plane are used to reconstruct an image by means of image reconstruction circuit 29 and image memory 31. Display unit 33 is used to display the reconstructed image.

According to the present invention, the subject 16 may be moved by means of bed 18 under the control of bed motion system 27 simultaneously with gantry rotation, such that the Z position of subject 16 is synchronized with angle of rotation of gantry 14. The direction of the motion of subject 16 may be along the Z axis or at oblique angles to the gantry 14 revolution plane; i.e., the X-Y plane. Furthermore, in the embodiment of the present invention, the rotating portions of gantry 14 may revolve continuously for more than one revolutions such as is possible with slip ring construction. The apparatus described hereinabove is particularly useful for performing helical scans.

The operation of the apparatus illustrated in FIG. 1b is the same as in FIG. 1a except that detector array 12 is mounted in the stationary part of the gantry and does not rotate. Detector elements are provided to cover at least an angular range of 180° around subject 16.

Figure 2B:
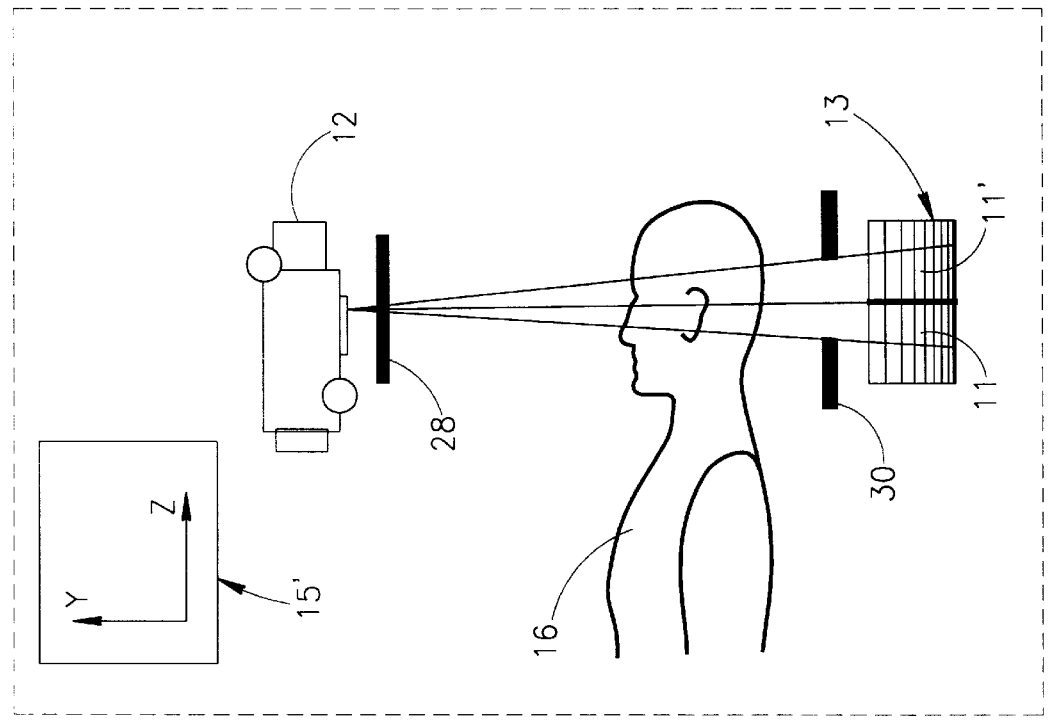
FIGS. 2a and 2b pictorially illustrate in views along the X axis and the Z axis; respectively, radiation source and detector elements extending in the axial or Z direction enabling the acquisition of multiple slice data from each source during a single rotation, as described in the above referred to U.S. patent application Ser. No. 915,459.
Figure 2A:
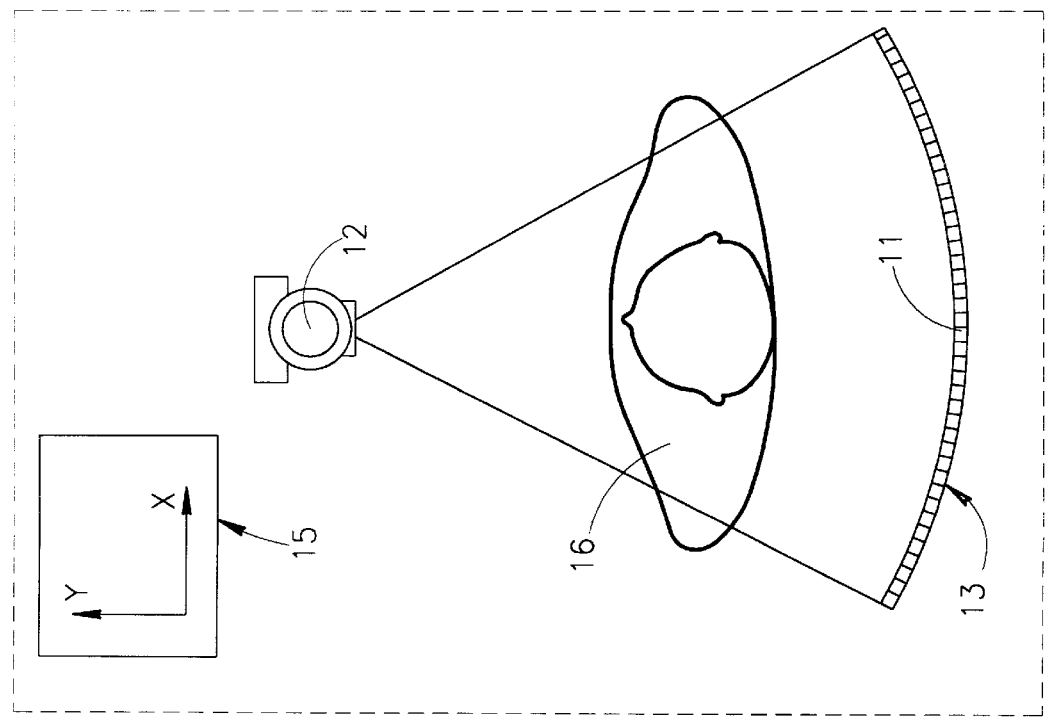

FIGS. 2a and 2b also illustrate the alternate arrangement of detector arrays 13 comprising multiple rows of detectors 11 and 11' which extend in the axial or Z direction.

Figure 3:
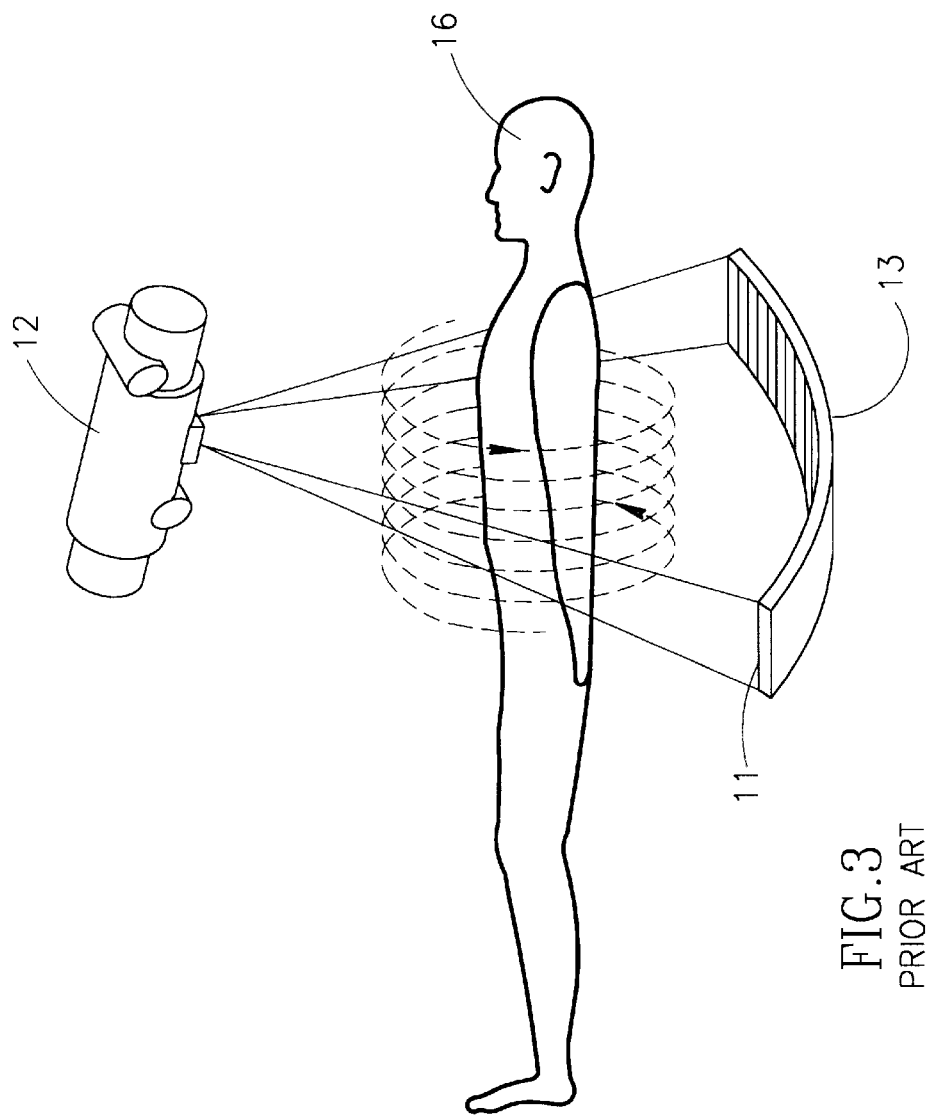
FIG. 3 pictorially illustrates one X-ray source and one array of a single detector element enabling the acquisition of spiral data adapting single slice, single source (prior art) methods.
Figure 3:
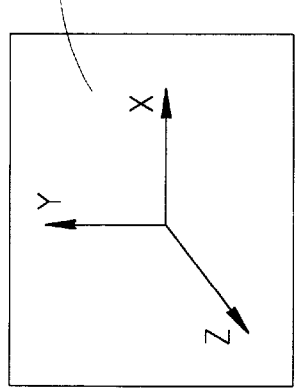

FIG. 3 illustrates the helical scans of prior art CT systems. Subject 16 moves along the Z axis while X-ray source 12 revolves about the subject. Fan shaped X-ray beams are detected by detector array 13 usually comprising a single row of detector elements 11. The X-ray beam in effect described a helix in its path about subject 16.

FIGS. 4a–4h illustrates helical scans performed by a multiple source, multi slice CT scanner described hereinabove. According to the present invention FIGS. 4a and 4b illustrate a 3rd generation scanner and FIGS. 4c–4e illustrate a 4th generation scanner. For simplicity, FIGS. 4a–4h illustrate the case of three sources of X-radiation arranged 120° apart in the same plane. In FIGS. 4a–4h the fan beam from source 12a forms an effective helix such as helix 17a (shown by dotted lines in FIG. 4a) about the subject 16 while the fan beam from source 12b forms another helix not shown in FIG. 4a about the subject 16 and the fan beam from source 12c forms another helix 17c, also not shown. Helices 17a, 17b, and 17c, are interleaved. It is apparent from FIG. 4a that in a general case of n X-ray sources there are n interleaved helices.

FIGS. 4f–4h illustrate further a multiple source—multiple slice CT scanner according to the present invention. In this particular embodiment, three sources of radiation 12a, 12b, 12c are arranged 120° apart in the same plane. Three detector element arrays, 13a, 13b and 13c are each divided in the Z direction to at least two rows of detector elements, thus providing at least six interleaved helices. It is obvious that the detector arrays may include more than two planes in the Z direction. Also, it is obvious that the sources are not limited to being separated by 120° and or in being in the same plane but may be arranged otherwise, within the scope of the invention. From FIG. 4a it is to be understood that the advantages of the system according to the present invention, as described hereinbelow, can be combined with the advantages of a multiple slice scanner as taught in the above referred to Patent Application.

The full width at half maximum (FWHM) of the slice sensitivity profile for a stationary-bed scan under given conditions is denoted hereinbelow as the nominal slice width. The FWHM of the slice sensitivity profile of the helical scan is denoted hereinbelow as the effective slice width.

It is desirable to have the effective slice width be as nearly equal to the nominal slice width as possible. However, helical scans tend to have an effective slice width larger than the nominal slice width. In general in single slice scanners the effective slice width becomes larger as the relative movement of the subject 16 increases (see FIG. 8). On the other hand, it is desirable for the relative movement of the subject 16 to be as large as feasible so as to scan a large volume in a short time.

According to one preferred embodiment of a system using the multiple X-ray source apparatus described hereinabove, the nominal slice width is considered the slice width obtained in a stationary-bed scan using each radiation source 12 and associated detector elements 11 for a single slice. This is the mode wherein multiple slices are acquired in a single scan. Helical scan image reconstruction involves interpolation of measurements made by detector elements 11 of the same rows and of different rows at different relative subject positions, responsive to radiation from the same radiation source in 3rd generation scanners or from different radiation sources 12 in 4th generation scanners.

Figure 5A:
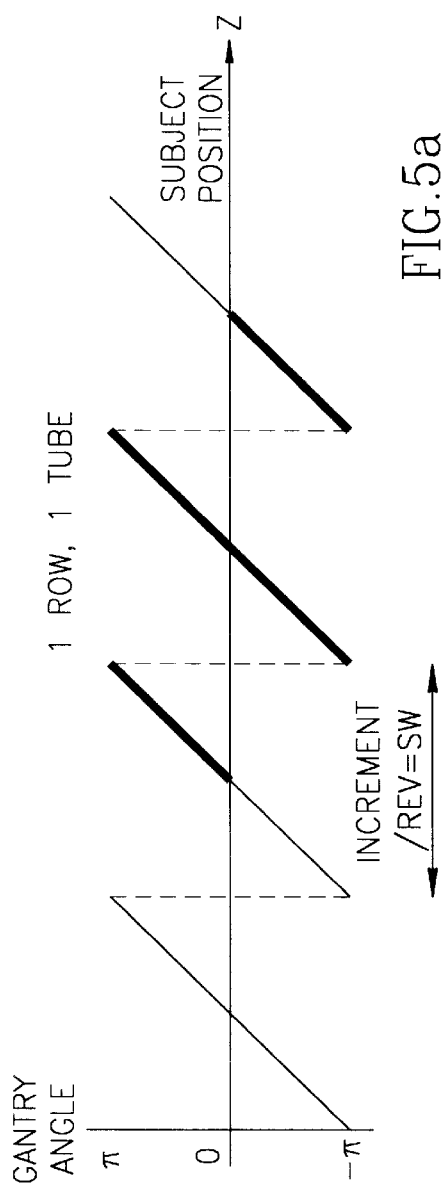
FIGS. 5a and 5b graphically and pictorially, respectively, illustrate the data acquired in a prior art helical scanner (FIG. 3), as the gantry rotates and the subject translates.
Figure 5B:
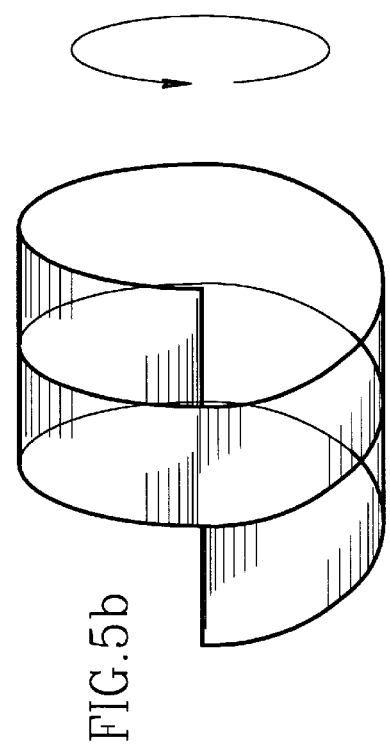
Figure 5C:
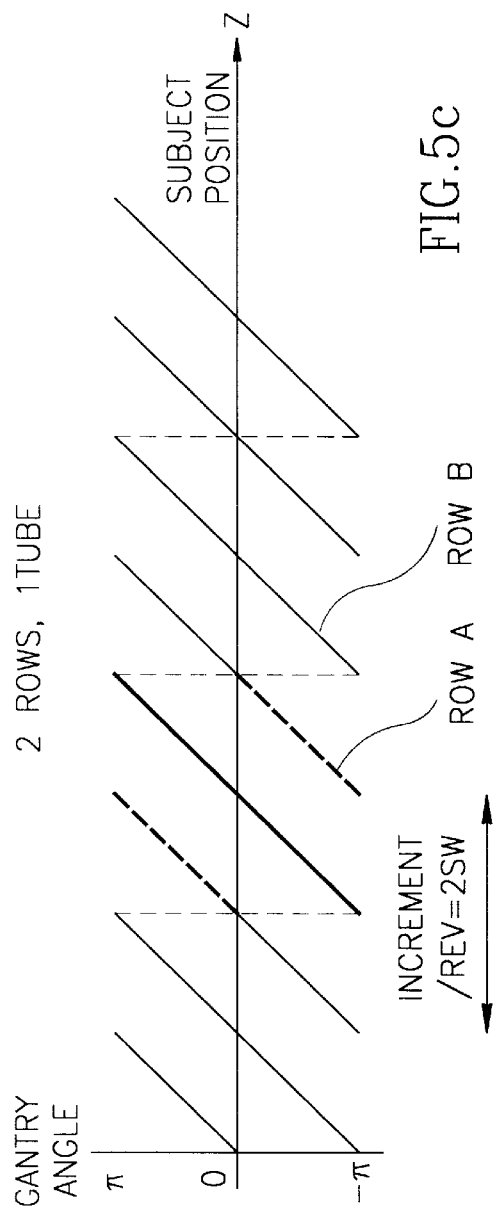
FIGS. 5c–5f graphically and pictorially illustrates the data acquired in a single source dual slice scanner according to U.S. Pat. No. 4,637,040.
Figure 6A:
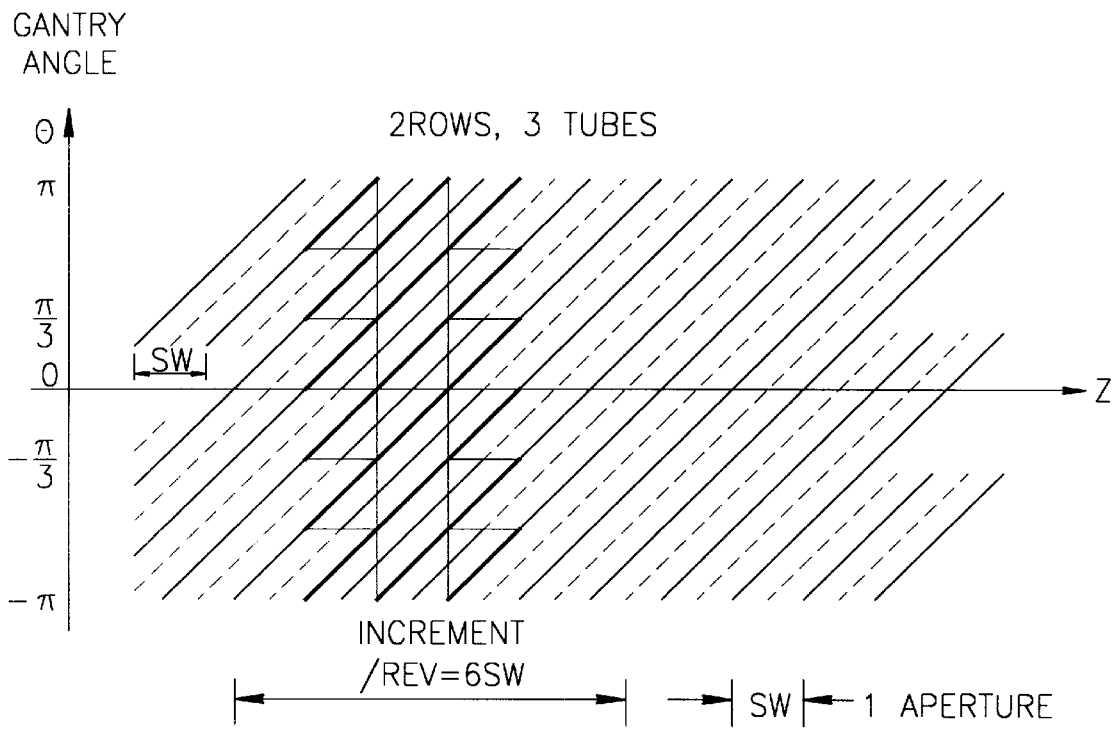
FIGS. 6a and 6b illustrate the data acquired in the inventive helical scanner with multiple slice data (3 arrays, each having 2 rows of detector elements) acquired per revolution being combined into single slices when the gantry rotates and the subject translates for a high velocity mode and an extra high resolution mode respectively.

FIGS. 5a and 5c graphically illustrate the gantry angle versus subject position in the prior art FIG. 3 in the system of U.S. Pat. No. 4,637,040 with m=2 and n=1. FIGS. 4a–4h illustrate certain advantages of the multiple slice helical scan system. The number of rows m of detector elements 11 in detector array 13 is described by way of example as m=2 and the number of radiation sources 12 is described by way of example as n=3. Effectively, data of identical quality may be acquired by the systems of FIG. 6a in one-sixth the time as that of the system of FIG. 5a where the speed of the subject motion in FIG. 6a is six times as great as in FIG. 5a. Thus, with a multiple source system it is possible to scan a longer section of the subject in a given time. Alternatively, if the two systems are used at the same subject speeds, a significantly increased amount of data of subject 16 is acquired using the system of FIG. 6b as compared to the amount of data acquired with the system of 5a. Thus, the system of FIG. 6b with the same subject speed as in the system of FIG. 5a yields images of a higher quality.

Figure 5D:
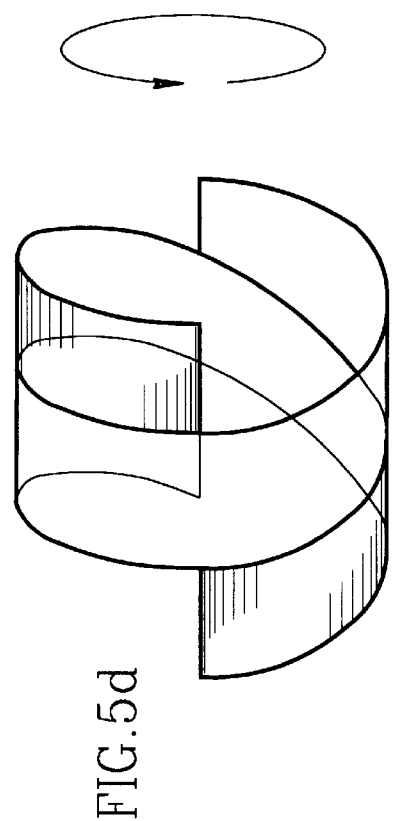
Figure 5E:
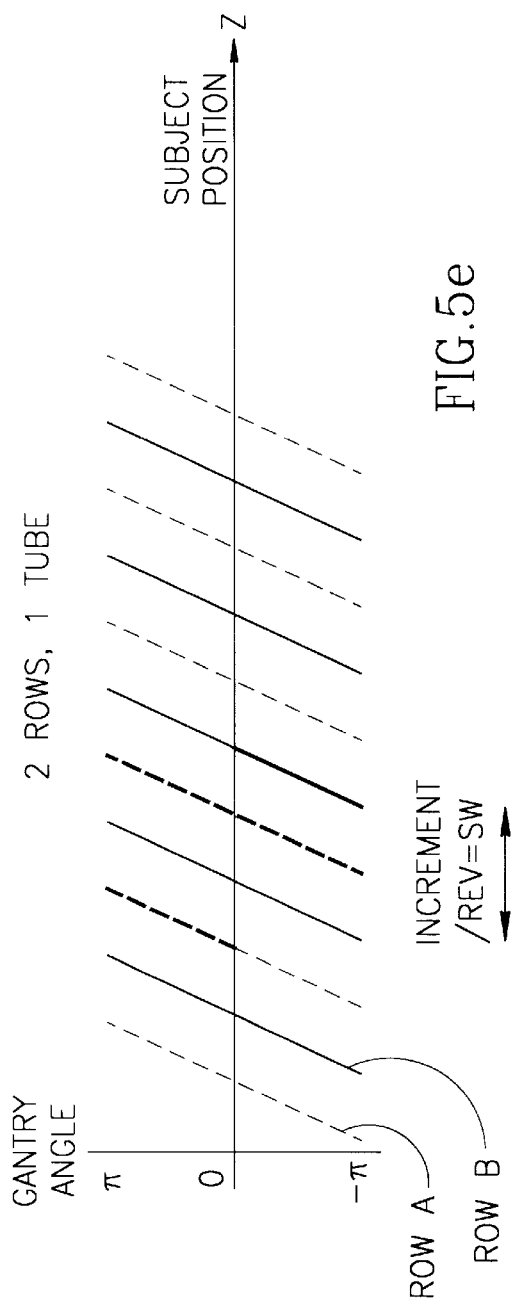
Figure 5F:
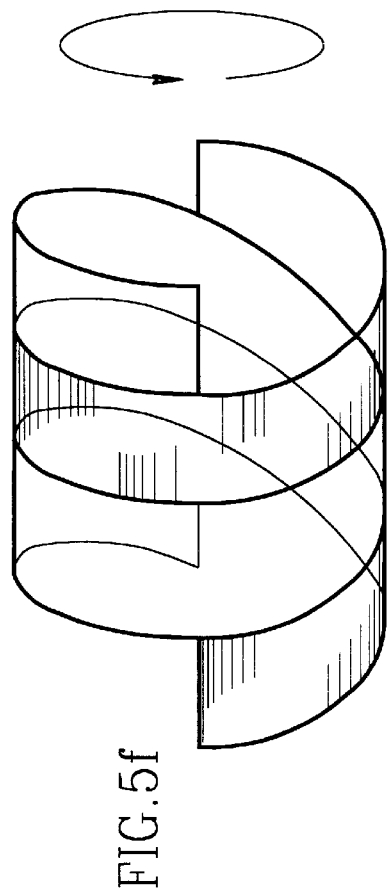

In the FIGS. 5a, 5c and 5e the segments of the helical scan in which useful data is obtained to reconstruct 360° images are schematically shown with heavy lines and pictorially shown as segments of helices in FIGS. 5b, 5d and 5f.

As illustrated in FIG. 5a relative to prior art for 360° reconstruction, data from the detector element in its previous 0 to 180 degree location and in its succeeding −180 to 0 degree location are interpolated (weighted interpolation) with the data of the slice being imaged to reformat the data into single data plane.

Figure 6B:
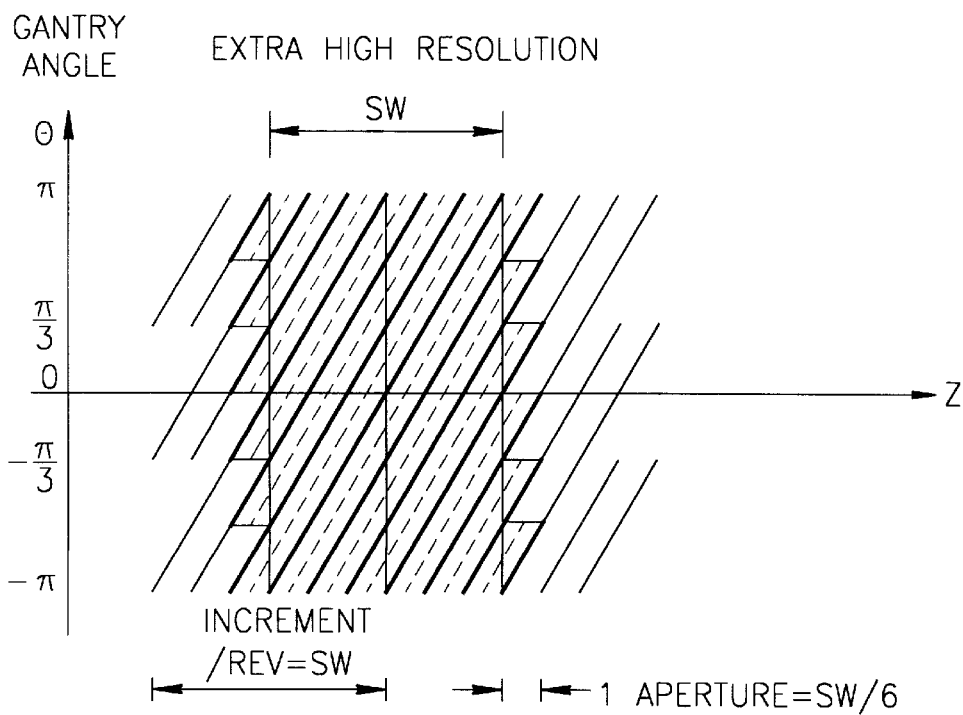

In FIGS. 6a and 6b the segments of the helical scan in which useful data is obtained to reconstruct 360° images are schematically shown with heavy lines in FIG. 6a and with dashed lines in FIG. 6b.

FIG. 6 illustrates that with the multiple source multi-slice helical scan more data is acquired. The interpolated planar data includes data from the detector elements used for one source in a given gantry rotation angle interpolated (weighted interpolation) with the data of the detector element acquiring intensity values from another source in the succeeding or previous 120 degree gantry position or with the data of the adjacent detector element acquiring intensity values simultaneously from the same source.

FIG. 6 graphically illustrates the gantry rotational angle versus subject 16 position in the system of FIG. 4f used as described herein. The number of sources 12 is, by way of example, set to n=3. The number of rows extending in the axial direction of detector elements 11 in detector array 13 is, by way of example, set to m=2. The number of adjacent rows used in reconstruction are explicitly set to n×m=2×3=6. Thus, the data of three sources and their two rows of detector elements are used as the data for a combined slice. It should be understood that each array can even have a different number of rows within the scope of this invention.

In FIG. 6a the segments of the helical scans from which useful data to reconstruct a 360° image are obtained are schematically shown by darkened lines. Thus, FIG. 6a shows that both slices A and B from every source are acquired. Data from the detector element imaging slice B in its previous 0 to 180 degree location and data from the detector element acquiring slices A in its succeeding −180 to 0 degree location are interpolated with the data from the detector element acquiring slices A and B. Then the data is used to provide a single image.

Figure 7:
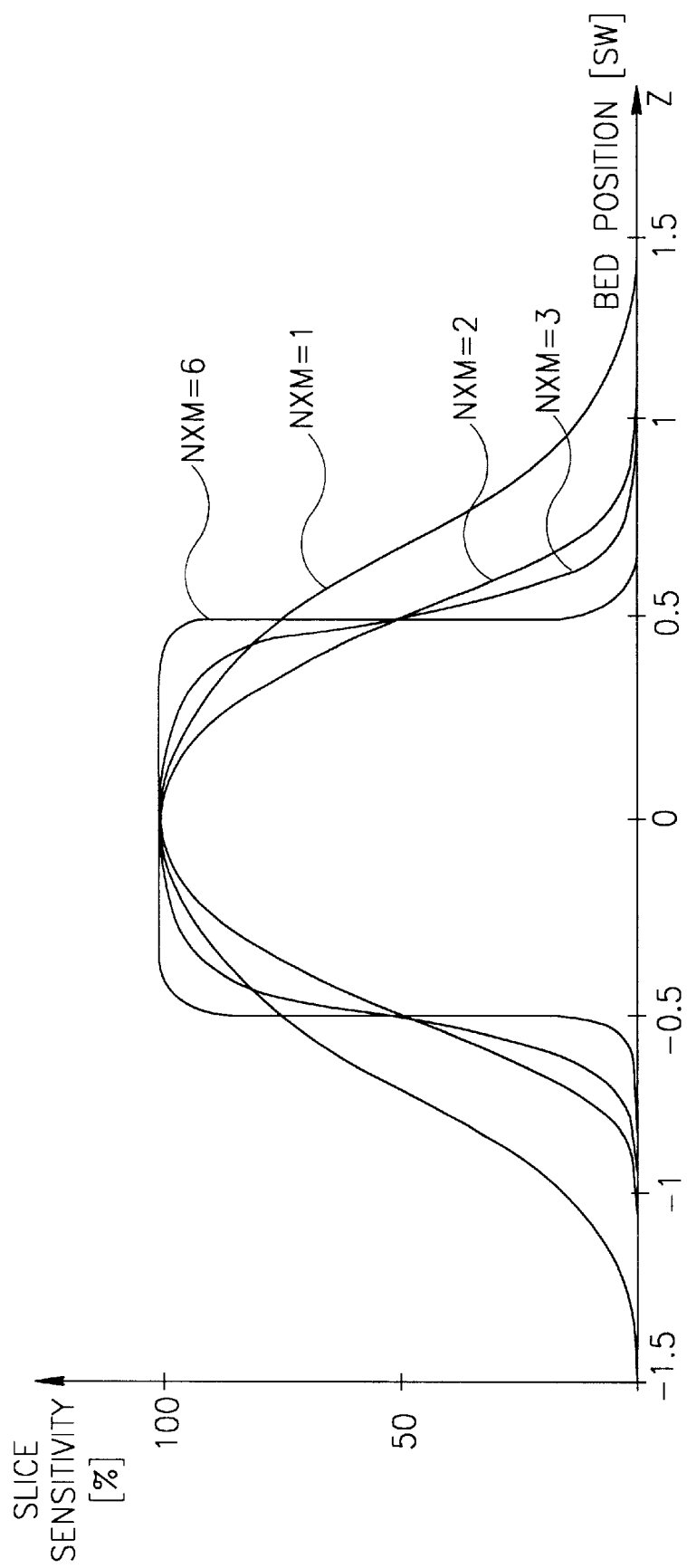
FIG. 7 graphically shows slice sensitivity profiles in the extra high resolution mode (FIG. 6b) as a function of position along the Z axis for different quantities of sources and/or rows of detector elements, and FIG. 8 graphically shows effective slice width per nominal slice width versus translation speed per revolution for different quantities (m) of axially extending detectors and/or different quantities (n) of X-ray sources.

FIG. 7 shows different slice sensitivity profiles each obtained according to the scheme of FIG. 6b with a different number n of sources and m of rows of detectors. The effective slice width discussed hereinabove is the FWHM of the curves in FIG. 7. For simplicity, a linear interpolation scheme between measurements at the same gantry angle and subject velocity of one nominal slice width per revolution of X-ray sources 12 is assumed. FIG. 7 shows graphically that the slice sensitivity profile becomes closer to rectangles as the number of slices increase. Therefore by increasing the number of sources, each associated with its own array of multi-row detectors the number of slices is most effectively increased.

Figure 8:
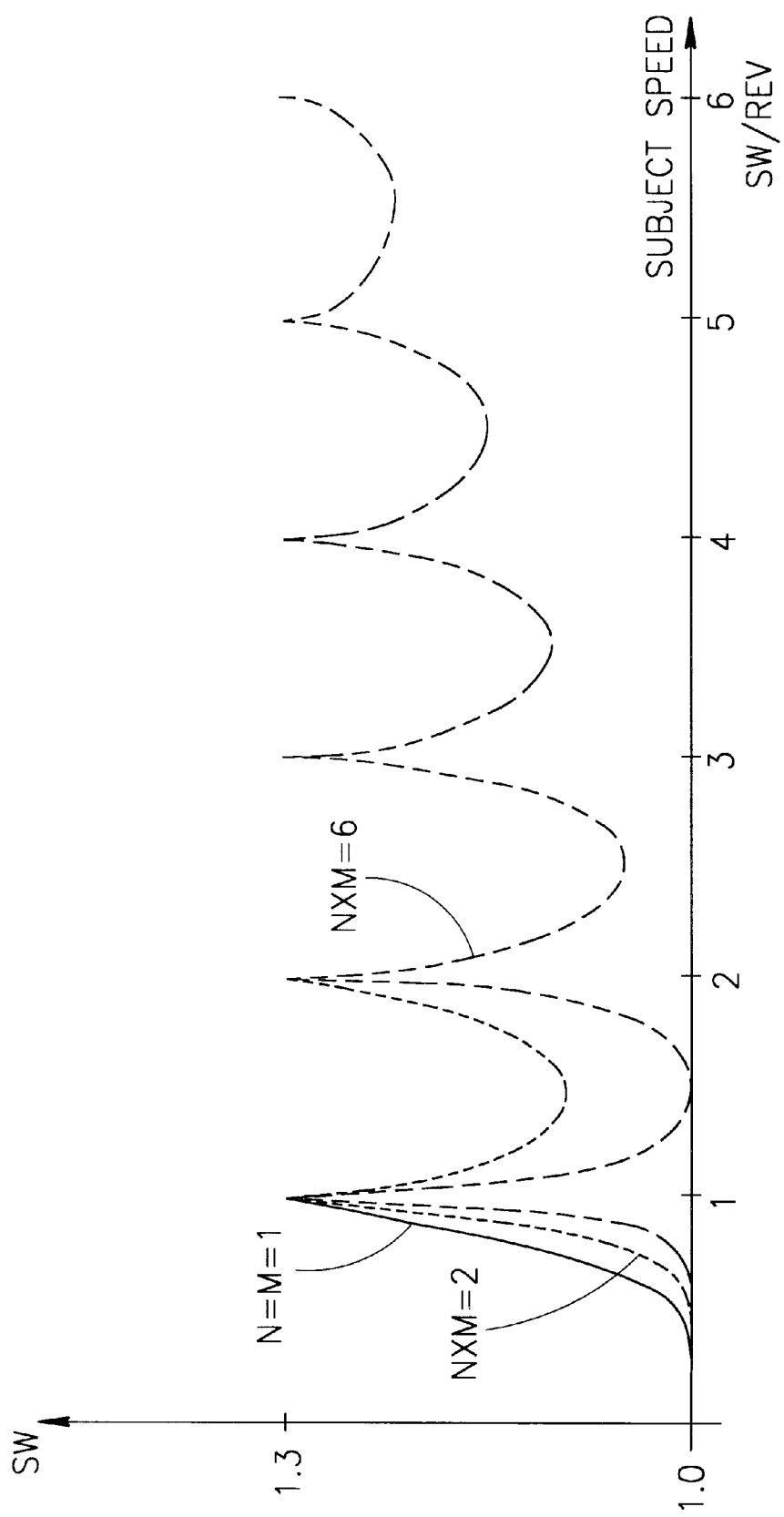

FIG. 8 illustrates the ratio of the effective slice width to nominal slice width as a function of the velocity of the subject 16 for the case of linear interpolation. The heavy solid line graph represents the prior art helical systems such as shown on FIG. 3. The dotted line graph represents a dual source single slice (or single source dual slice) system. The dashed line graph represents a six source single slice system or triple source, dual slice helical system such as illustrated in FIG. 4a or 4f.

FIG. 8 indicates that on a multiple source CT scanner a higher subject 16 velocity is possible than on a single source CT scanner with the same or even an improved slice sensitivity profile. Therefore, with multiple source CT, a given volume of subject 16 may be scanned in a shorter time. In particular, on a "n" source, single slice CT scanner with a relative velocity for subject 16 of n nominal slice widths per revolution of the gantry 14, the effective slice width is the same as obtained for a single source single slice CT scanner at a subject 16 velocity of one nominal slice width per revolution of the gantry. On an "n" source "m" slice CT scanner with a velocity for the subject 16 of n×m nominal slice widths per revolution of the gantry, the effective slice width is the same as obtained for a single source single slice CT scanner at a subject velocity of one nominal slice width per revolution. Both n and m are equal to positive integers.

According to another preferred embodiments of a system using the multiple slice CT scanner described hereinabove, the nominal slice width is considered the combined slice width obtained in a stationary-bed scan using data of multiple rows of detector elements 11 added together for a single combined slice.

Helix image reconstruction involves interpolation of data measured simultaneously by the detector elements of n adjacent sources each associated with m adjacent rows of detector elements and the data measured simultaneously or at a different time by another detector element of one of the m rows or an adjacent row.

FIGS. 7–8 illustrate, for reasons of simplicity, a linear interpolation scheme between measurements at the same gantry angle and constant bed speed. Those familiar with the art of computerized tomography will appreciate that there is an advantage in using the embodiments described hereinabove over prior art for almost any interpolation scheme and/or bed velocity scheme.

Returning again to FIG. 1, according to the present invention, another preferred embodiment using the multiple slice CT scanner described hereinabove includes the capability of continuous rotation through a partial revolution of the multi-slice CT scanner about subject 16 but does not require simultaneous motion of subject 16. The partial revolution must be at least 1/n revolution; where n is the number of sources. According to this embodiment, intensity data for X-rays from X-ray sources 12a, 12b and 12c which have traversed multiple planar sections through subject 16 are measured simultaneously during continuous rotation through partial revolutions of gantry 14 while bed 18 is stationary. Data obtained from X-rays emitted by the same or different sources i.e. 12(a) and/or 12(b) measured at the same gantry angle are averaged and used in reconstruction to yield multiple images which have the statistics level of a long exposure, but are generally free from motion related artifacts.

The advantage of this embodiment over the prior art is that multiple planar sections of subject 16 are simultaneously scanned to obtain multiple images. The simultaneous scanning acquires data due to the plurality of X-ray sources and the plurality of detector elements that are used to obtain data form the same projections. Accordingly, simultaneous scanning reduces the time of the study thereby canceling the increased time and compensating for the increased load of X-ray sources 12a, 12b and 12c associated with multiple revolution scans.

Alternatively, in yet another preferred embodiment of the present invention, the data from adjacent planar sections of the multiple planar sections measured simultaneously during one revolution of the gantry are combined and single images are reconstructed corresponding to planar sections having substantially the combined width of the individual multiple planar sections which are generally free from partial volume artifacts.

Finally, the two preferred embodiments described immediately hereinabove may be combined to form a CT scanner system wherein single images which are generally free from motion and partial volume artifacts are reconstructed from combined multiple planar section data acquired in multiple gantry revolutions.

Alternatively, in yet another preferred embodiment of the present invention, at least one of the X-ray sources activate with different voltage so as to achieve an ability to distinguish between very close organs with the same average attenuation coefficient for one X-ray energy but with different average attenuation coefficients to different X-ray energy.

Persons skilled in the art of X-ray detection will appreciate that the present invention is not limited to a particular detector array, but rather to any apparatus that yields the intensity and position of the X-rays. In particular, detector arrays 13a, 13b and 13c may comprise multiple detector elements, multiple segmented detector elements, an array of single detectors or a continuous media responsive to X-rays that also provides position readouts.

Although the invention has been described with reference to particular embodiments the invention is not confined to the specific embodiments described hereinabove but rather to the general scope of the claims.

What is claimed is:

1. A CT scanner system comprising:
   a gantry,
   a bed for supporting a scanned subject within an aperture in said gantry,
   a plurality of x-ray sources mounted on said gantry,
   a gantry rotation system for revolving said x-ray sources about said subject,
   an x-ray detector array,
   said detector array comprising an x-ray detector group associated with each of said sources on the side of the subject opposite from said x-ray sources, said detector groups comprising multiple rows of detector elements extending in the axial direction,
   said detector array detecting x-rays that have originated from the x-ray sources and traversed at least one planar section of said subject to acquire radiation intensity data,
   a motion system for causing relative motion in an axial direction between said gantry and said subject during the scan so that said data is acquired by said detector array while said x-ray sources revolve about said subject and during the relative motion along said axial direction to provide a helical scan,
   an image reconstruction system for generating images from said data where said reconstruction system includes a reformatting system for reformatting multiple plane data into single plane data, and
   said reformatting system comprising circuitry for combining data acquired by a given detector element of one row at a given gantry angle with data acquired by another detector element adjacent to the detector element of the said one row at the given gantry angle that is associated with the same x-ray source.

2. The CT scanner system of claim 1 wherein said detector array detects x-rays that emanate simultaneously from the x-ray sources.

3. A CT scanner system comprising:
   a gantry,
   a bed for supporting a scanned subject within an aperture in said gantry,
   a plurality of x-ray sources mounted on said gantry,
   a gantry rotation system for revolving said x-ray sources about said subject,
   an x-ray detector array comprising a plurality of detector elements for detecting x-rays that have passed through the subject,
   said x-ray detector array comprising an x-ray detector group associated with each of said x-ray sources on the side of the subject opposite from said x-ray sources,
   said detector groups comprising multiple rows of detector elements extending in the axial detection,
   said detector array detecting x-rays that have originated from the x-ray sources and traversed at least one planar section of said subject to acquire radiation intensity data,
   a motion system for causing relative motion in an axial direction between said gantry and said subject during the scan so that data is acquired by said detector array while said x-ray sources revolve about said subject and during said relative motion in said axial direction to provide a helical scan,
   an image reconstruction system for generating images from said data where said reconstruction system includes a reformatting system for reformatting multiple plane data into single plan data, and
   said reformatting system comprising circuitry for combining first data acquired by a detector element of a first of said x-ray detector groups associated with a first of said x-ray sources said detector element being at a given row and given gantry angle, with other data acquired by another detector element of another of said x-ray detector groups associated with another x-ray source, said another detector element being at a row and gantry angle corresponding to said given row and given gantry angle.

4. The CT scanner system of claim 3 wherein said reformatting system comprises circuitry for interpolating data acquired by a detector element at a given gantry angle with data acquired by another detector element in the same one of said multiple rows at the given gantry angle but associated with another x-ray source.

5. A CT scanner system comprising:
   a gantry,
   a bed for supporting a scanned subject within an aperture in said gantry,
   a plurality of individual x-ray sources mounted on said gantry spaced apart from each other,
   a gantry rotation system for revolving said x-ray sources about said subject,
   an x-ray detector array comprising multiple rows extending in an axial direction, each of said rows including a plurality of detector elements for detecting x-rays that have passed through the subject, said detector array detecting x-rays that have originated from the x-ray sources and have traversed at least one planar section of said subject to thereby acquire radiation intensity data, a motion system for causing relative motion in an axial direction between said gantry and said subject during the scan so that said data is acquired by said detector array while said x-ray sources revolve about said subject and during the relative motion along said axial direction to provide a helical scan, an image reconstruction system for generating images from said data where said reconstruction system includes a reformatting system for reformatting multiple plane data into a single plane data, and said reformatting system comprising circuitry for interpolating data acquired simultaneously by adjacent detector elements each in one of said multiple rows and at a given gantry angle.

6. A CT scanner system comprising:

a gantry, a bed for supporting a scanned subject within an aperture in said gantry, a plurality of x-ray sources mounted on said gantry, a gantry rotation system for revolving said x-ray sources about said subject, an x-ray detector array, said x-ray detector array comprising an x-ray detector group associated with each of said sources on the side of the subject opposite from said x-ray sources, said detector groups comprising multiple rows of detector elements extending in an axial direction, for detecting x-rays that have passed through the subject, said detector array detecting x-rays that have originated from the x-ray sources and have traversed at least one planar section of said subject to acquire radiation intensity data, a motion system for causing relative motion in an axial direction between said gantry and said subject during the scan so that said data is acquired by said detector array while said x-ray sources revolve about said subject and during the relative motion along said axial direction to provide a helical scan, an image reconstruction system for generating images from said data where said reconstruction system includes a reformatting system for reformatting multiple plane data into single plane data, and said multiple rows including different numbers of detector elements per row.

7. A CT scanner system comprising:

a gantry, a bed for supporting a scanned subject within an aperture in said gantry, a plurality of x-ray sources mounted on said gantry, a gantry rotation system for revolving said x-ray sources about said subject, an x-ray detector array comprising a plurality of detector elements for detecting x-rays that have passed through the subject, said detector array detecting x-rays that have originated from the x-ray sources and traversed at least one planar section of said subject to thereby acquire radiation intensity data, a motion system for causing relative motion in said axial direction between said gantry and said subject during the scan so that said data is acquired by said detector array which said x-ray sources revolve about said subject and during the relative motion along said axial direction to provide a helical scan, an image reconstruction system for generating images from said data where said reconstruction system includes a reformatting system for reformatting multiple plane data into single plane data, and wherein circuitry for controlling said detector array to nutate is included.

8. A CT scanner system comprising:

a gantry, a bed for supporting a scanned subject within an aperture in said gantry, a plurality of individual x-ray sources mounted on said gantry spaced apart from each other, a gantry rotation system for revolving said x-ray sources about said subject, an x-ray detector array comprising a plurality of rows of detector elements extending in an axial direction for detecting x-rays that have passed through the subject, said detector array detecting x-rays that have originated from x-ray sources and traversed at least one planar section of said subject to thereby acquire radiation intensity data, a motion system for causing relative motion in an axial direction between said gantry and said subject during the scan so that said data is acquired by said detector array while said x-ray sources revolve about said subject and during the relative motion along said axial direction to provide a helical scan, an image reconstruction system for generating images from said data where said reconstruction system includes a reformatting system for reformatting multiple plane data into a single plane data, and said reformatting system comprising circuitry for combining data acquired by a detector element at a given gantry angle with data acquired by the same detector element at the given angle but associated with another of the individual x-ray sources.

9. The CT system of claim 8 wherein said means for combining comprises means for interpolating.

10. A CT scanner system comprising:

a gantry, a bed for supporting a scanned subject within an aperture in said gantry, a plurality of x-ray sources mounted on said gantry, a gantry rotation system for revolving said x-ray sources about said subject, an x-ray detector array, said detector array comprising an x-ray detector group associated with each of said sources on the side of the subject opposite from said x-ray sources, said detector groups comprising multiple rows of detector elements extending in the axial direction, said detector array detecting x-rays that have originated from the x-ray sources and traversed at least one planar section of said subject to acquire radiation intensity data, a motion system for causing relative motion in an axial direction between said gantry and said subject during the scan so that said data is acquired by said detector array while said x-ray sources revolve about said subject and during the relative motion along said axial direction to provide a helical scan, an image reconstruction system for generating images from said data where said reconstruction system includes a reformatting system for reformatting multiple plane data into single plane data, and means for reconstructing images from said scan using interpolation between data from the acquired multiple planar sections acquired by a detector array associated with a first radiation source, and data from the acquired multiple planar sections acquired by a detector array that is associated with a different radiation source.

11. The CT scanner system of claim 10 wherein said interpolation between data is linear as a function of bed position.

12. The CT scanner system of claim 10 wherein said interpolation between data is non-linear as a function of bed position.

13. A CT scanner system comprising:

a gantry, a bed for supporting a scanned subject within an aperture in said gantry, a plurality of x-ray sources mounted on said gantry, a gantry rotation system for revolving said x-ray sources about said subject, an x-ray detector array comprising a plurality of detector elements for detecting x-rays that have passed through the subject, said detector array detection x-rays that have originated from the x-ray sources and traversed at least one planar section of said subject to thereby acquire radiation intensity data, a motion system for causing variable relative motion in an axial direction between said gantry and said subject during the scan so that said data is acquired by said detector array while said x-ray sources revolve about said subject and during the variable relative motion along said axial direction to provide a helical scan, and an image reconstruction system for generating images from said data wherein said reconstruction system includes a reformatting system for reformatting multiple plane data into single plane data.

14. A method of CT scanning of a subject comprising:

mounting a plurality of individual x-ray sources on a gantry spaced apart from each other;

supporting a subject on a bed within an aperture in said gantry, revolving said x-ray sources about said subject, detecting x-rays from each of said plurality of individual sources that have traversed multiple planar sections of said subject to acquire radiation intensity data, causing relative motion in an axial direction between said gantry and said subject while said x-ray source revolves about the subject to provide a helical scan, reconstructing images from said data where said reconstruction includes reformatting into plane data, and wherein said reformatting comprises interpolating data acquired by a detector element of one row of said multiple rows at a given gantry angle and data acquired by another detector element at the given gantry angle in another row.

15. A method of CT scanning of a subject comprising:

mounting a plurality of individual x-ray sources on a gantry spaced apart from each other, with at least one of said plurality of x-ray sources having multiple focal spots, mounting a plurality of x-ray detector arrays on said gantry, each of said detector arrays associated with one of said x-ray sources, supporting a subject on a bed within an aperture in said gantry, revolving said x-ray sources and said detector arrays about said subject, detecting x-rays from each of said plurality of sources that have traversed multiple planar sections of said subject to acquire radiation intensity data, causing relative motion in an axial direction between said gantry and said subject while said x-ray source revolves about the subject to provide a helical scan, and reconstructing images from said data where said reconstruction includes reformatting said data into plane data.

16. A method of CT scanning of a subject comprising:

mounting a plurality of individual x-ray sources on a gantry, spaced apart from each other, mounting a plurality of detector arrays on said gantry, each detector array being individual to one of said x-ray sources and including rows of detectors extending axially, supporting a subject on a bed within an aperture in said gantry, revolving said x-ray sources about said subject, energizing said plurality of x-ray sources to emit x-rays simultaneously, detecting x-rays from each of said plurality of sources that have traversed multiple planar sections of said subject to acquire planar section radiation intensity data, reconstructing images from said scan by interpolating between data acquired from said multiple planar sections, and acquiring said data simultaneously from detectors in adjacent rows.

17. A method of CT scanning of a subject comprising:

mounting a plurality of x-ray sources on a gantry, supporting a subject on a bed within an aperture in said gantry, revolving said x-ray sources about said subject, detecting x-rays from each of said plurality of sources that have traversed multiple planar sections of said subject to acquire radiation intensity data, causing relative motion having variable velocity in an axial direction between said gantry and said subject while said x-ray sources revolve about the subject to provide a helical scan, and reconstructing images from said data where said reconstruction includes formatting into plane data.

18. A CT scanner system comprising:

a gantry, a bed for supporting a scanned subject within an aperture in said gantry, a plurality of individual x-ray sources mounted on said gantry spaced apart from each other, a gantry rotation system for revolving said x-ray sources about said subject, an x-ray detector array individual to each of the sources comprising a plurality of detector elements for detecting x-rays that have passed through the subject, said detector array detecting x-rays that have originated from the x-ray sources and traversed at least one planar section of said subject to thereby acquire radiation intensity data, a motion system for causing relative motion in said axial direction between said gantry and said subject during the scan so that said data is acquired by said detector array while said x-ray sources revolve about said subject and during the relative motion along said axial direction to provide a helical scan, an image reconstruction system for generating images from said data where said reconstruction system includes a reformatting system for reformatting multiple plane data into single plane data, and wherein said detector array comprises segmented detector elements.

19. The CT system according to claim 18 where at least one of said x-ray sources has multiple focal spots.

20. A method of CT scanning of a subject comprising:

mounting a plurality of individual x-ray sources on a gantry, spaced apart from each other;

mounting a plurality of detector arrays on said gantry with each of the arrays associated with one of said x-ray sources, supporting a subject on a bed within an aperture in said gantry, revolving said x-ray sources and detector arrays about said subject, detecting x-rays from each of said plurality of sources that have traversed multiple planar sections of said subject to acquire radiation intensity data, causing relative motion in an axial direction between said gantry and said subject while said x-ray source revolves about the subject to provide a helical scan, reconstructing images from said data where said reconstruction includes reformatting into plane data, and wherein said reformatting comprises interpolating data acquired by selected detector elements near a point whose value is being determined.

21. The method of CT scanning of claim 20 and nutating said detector array.

22. The method of CT scanning according to claim 20 wherein said interpolating includes linearly interpolating said data as a function of subject position.

23. The method of CT scanning according to claim 20 wherein said interpolating includes non-linearly interpolating said data as a function of subject position.

24. A method of CT scanning including the steps of:

supporting a scanned subject in an arbitrary position within an aperture of a gantry, mounting a plurality of x-ray sources on said gantry, rotating said plurality of x-ray sources about said subject more than 1/n revolutions where n is the number of x-ray sources, mounting an x-ray detector on the side of said subject opposite to each of said plurality of x-ray sources, simultaneously detecting x-rays with said detectors that have traversed multiple planar sections in said subject during the rotating step, averaging the data detected at the same angle of rotation of at least one of said plurality of x-ray sources during a continuous rotation through at least a partial revolution of said x-ray sources, and reconstructing multiple images corresponding to planar sections measured simultaneously by said detected arrays, said images being reconstructed from said averaged data of multiple partial rotations of said x-ray source.

25. The method of CT scanning of claim 24 including controlling said plurality of x-ray sources to emit x-rays simultaneously.

26. A CT system including:

a gantry, a bed for supporting a scanned subject in an arbitrary position within an aperture of said gantry, individual multiple x-ray sources on said gantry, a gantry rotating system for rotating said x-ray sources at a substantially constant speed about said subject for at least one continuous revolution, an x-ray detector array on the side of said subject opposite each of said x-ray sources, said detector array comprising detector elements arranged for simultaneously detecting x-rays that have traversed multiple planar sections in said subject, a data acquisition system for combining data detected at the same gantry angle during consecutive revolutions of said x-ray source, and an image reconstructing system for reconstructing multiple images corresponding to planar sections measured simultaneously by said detector arrays, said images being reconstructed from combined data of multiple revolutions of said x-ray source.

27. The CT system of claim 26 including controls for causing said x-ray sources to simultaneously emit x-rays.

28. The CT system of claim 26 wherein said detector array comprises a detector group arranged opposite each of said x-ray sources and rotating therewith.

29. A method of CT scanning including:

supporting a scanned subject within an aperture of a gantry, mounting a plurality of x-ray sources on said gantry, revolving said plurality of x-ray sources about said subject, mounting an x-ray detector array on the side of said subject opposite to each of said plurality of x-ray sources, simultaneously acquiring image data with said detector arrays from x-rays that have traversed multiple plane sectors in said subject, combining the data received from adjacent planar sections of said multiple planar sections, reconstructing single images corresponding to planar sections with substantially the combined width of said multiple planar sections added together, and wherein the combining step comprises averaging.

30. A method of CT scanning including:

supporting a scanned subject within an aperture of a gantry, mounting a plurality of x-ray sources on said gantry, revolving said plurality of x-ray sources about said subject, mounting an x-ray detector array on the side of said subject opposite to each of said plurality of x-ray sources, simultaneously acquiring image data from x-rays with said detector arrays which x-rays have traversed multiple planar section in said subject, combining the data received from adjacent planar sections of said multiple planar sections, and reconstructing different images from the same bed position by using different effective x-ray energies.

31. A method of CT scanning including:

supporting a scanned subject within an aperture of a gantry, mounting a plurality of x-ray sources on said gantry, revolving said plurality of x-ray sources about said subject, mounting an x-ray detector array on the side of said subject opposite to each of said plurality of x-ray sources, simultaneously acquiring image data from x-rays with said detector arrays which x-rays have traversed multiple planar section in said subject, combining the data received from adjacent planar sections of said multiple planar sections, and reconstructing different images in a spiral scan by taking data for reconstruction using different x-ray radiation energies in the different sources.

32. A CT system including:

a gantry, a bed for supporting a scanned subject in an arbitrary position within an aperture of said gantry, multiple x-ray sources mounted on said gantry, an x-ray detector array mounted on the said gantry on the side of said subject opposite to said multiple x-ray sources to detect x-rays from said multiple sources that have traversed said subject, said detector array comprising detector elements arranged to detect x-rays that have traversed multiple planar sections in said subject, a data acquisition system for averaging data received from adjacent planar sections detected at the same gantry angles during consecutive revolutions of said x-ray source, and an image reconstruction system for reconstruction of single images corresponding to planar sections with substantially the combined width of the multiple planar sections added together.

33. The CT system of claim 32 including controls for energizing the x-ray sources to simultaneously emit x-rays.

34. The system of claim 32 wherein said x-ray detector array comprises an x-ray detector array group mounted opposite each of said multiple x-ray sources and rotating therewith.

35. The system according to claim 32 and means for applying at least two different voltages to different ones of said plurality of x-ray sources.

36. A CT scanner system comprising:

a gantry, a bed for supporting a scanned subject within an aperture in said gantry, a plurality of individual x-ray sources non-symmetrically mounted on said gantry spaced apart from each other, a gantry rotation system for revolving said x-ray sources about said subject, an x-ray detector array individual to each of the individual sources comprising a plurality of detector elements for detecting x-rays that have passed through the subject, said detector array detecting x-rays that have originated from the x-ray sources and traversed at least one planar section of said subject to thereby acquire radiation intensity data, a motion system for causing relative motion in an axial direction between said gantry and said subject during the scan so that said data is acquired by said detector array while said x-ray sources revolve about said subject and during the relative motion along said axial direction to provide a helical scan, and an image reconstruction system for generating images from said data where said reconstruction system includes a reformatting system for reformatting a multiple plane data into single plane data.

* * * * *